(12) United States Patent
Liu et al.

(10) Patent No.: US 9,320,477 B2
(45) Date of Patent: Apr. 26, 2016

(54) METHOD AND APPARATUS FOR ADAPTIVE SCATTER CORRECTION

(75) Inventors: Xin Liu, Waukesha, WI (US); Jiang Hsieh, Brookfield, WI (US); Xiaoye Wu, Rexford, NY (US)

(73) Assignee: General Electric Company, Schenectady, NY (US)

( * ) Notice: Subject to any disclaimer, the term of this patent is extended or adjusted under 35 U.S.C. 154(b) by 531 days.

(21) Appl. No.: 13/223,803

(22) Filed: Sep. 1, 2011

(65) Prior Publication Data

US 2013/0058450 A1    Mar. 7, 2013

(51) Int. Cl.
*A61B 6/03* (2006.01)
*A61B 6/00* (2006.01)

(52) U.S. Cl.
CPC .............. *A61B 6/032* (2013.01); *A61B 6/5282* (2013.01); *A61B 6/482* (2013.01)

(58) Field of Classification Search
CPC ........ A61B 6/03; A61B 6/032; A61B 6/5282; A61B 6/583; A61B 6/483; G06T 11/005
USPC ............................................... 378/7; 382/131
See application file for complete search history.

(56) References Cited

U.S. PATENT DOCUMENTS

| | | | | |
|---|---|---|---|---|
| 5,615,279 A | * | 3/1997 | Yoshioka et al. | 382/131 |
| 5,666,391 A | * | 9/1997 | Ohnesorge et al. | 378/7 |
| 7,283,605 B2 | | 10/2007 | Sainath et al. | |
| 2003/0138074 A1 | * | 7/2003 | Bruder | 378/4 |
| 2009/0092219 A1 | * | 4/2009 | Wu et al. | 378/5 |
| 2009/0290682 A1 | * | 11/2009 | Star-Lack et al. | 378/87 |

FOREIGN PATENT DOCUMENTS

| | | | |
|---|---|---|---|
| JP | 11028203 A | * | 2/1999 |
| JP | 2009106433 A | * | 5/2009 |

OTHER PUBLICATIONS

Star-Lack et al., Efficient scatter correction using asymmetric kernels, Conference date Feb. 9, 2009, Medical imaging 2009, Physics of Medical Imaging, SPIE, vol. 7258, pp. 1Z-1 to 1Z-12.*
Hsieh, Computed Tomography Principles, Design, Artifacts and Recent Advances, 2009, ISBN 978-0-8194-7533-6, pp. 231-235.*
Lui, Scattered Photon Transport Simulation in X-ray Imaging Systems, Nov. 2012, Transactions of the American Nuclear Society, vol. 107, pp. 570-571.*

(Continued)

*Primary Examiner* — David J Makiya
*Assistant Examiner* — John Corbett
(74) *Attorney, Agent, or Firm* — Dean D. Small; The Small Patent Law Group, LLC

(57) ABSTRACT

A CT system includes a rotatable gantry having an opening to receive an object to be scanned, an x-ray source configured to project an x-ray beam toward the object having a primary intensity, a detector configured to detect high frequency electromagnetic energy passing through the object and output imaging data, and a data acquisition system (DAS) connected to the detector and configured to receive the imaging data. The system also includes a computer programmed to obtain image projection data of the object from the DAS, correct the projection data using a scatter function that is based at least on a known characteristic of the x-ray beam, and generate images using the corrected projection data.

27 Claims, 6 Drawing Sheets

(56) References Cited

OTHER PUBLICATIONS

Kruger et al., A regional convolution kernel algorithm for scatter correction in dual-energy images: Comparison to single-kernel algorithms, 1994, Medical Physics, vol. 21, No. 2, pp. 175-184.*

Hinshaw et al., Recent progress in noise reduction and scatter correction in dual-energy imaging, 1995, SPIE, vol. 2432, pp. 134-142.*

Molloi et al., Scatter-glare corrections in quantitative dual-energy fluoroscopy, 1988, Medical Physics, vol. 15, No. 3, pp. 289-297.*

PTO-13-5937 which is a translation of JP2009106433A.*

Hangartner, Correction of scatter in computed tomography images of bone, 1987, Medical Physics, vol. 14, No. 3, pp. 335-340.*

Ohnesorge et al., Efficient object scatter correction algorithm for third and fourth generation CT scanners, 1999, European Radiology, vol. 9, pp. 563-569.*

Ohnesorge et al., "Efficient object scatter correction algorithm for third and fourth generation CT scanners," European Radiology, 1999, vol. 9, pp. 563-569.

* cited by examiner

METHOD AND APPARATUS FOR ADAPTIVE SCATTER CORRECTION

BACKGROUND OF THE INVENTION

Embodiments of the invention relate generally to diagnostic imaging and, more particularly, to a method and apparatus for adaptive scatter correction in an imaging system.

Typically, in computed tomography (CT) imaging systems, an x-ray source emits a fan-shaped beam toward a subject or object, such as a patient or a piece of luggage. Hereinafter, the terms "subject" and "object" shall include anything capable of being imaged. The beam, after being attenuated by the subject, impinges upon an array of radiation detectors. The intensity of the attenuated beam radiation received at the detector array is typically dependent upon the attenuation of the x-ray beam by the subject. Each detector element of the detector array produces a separate electrical signal indicative of the attenuated beam received by each detector element. The electrical signals are transmitted to a data processing system for analysis which ultimately produces an image.

Generally, the x-ray source and the detector array are rotated about the gantry within an imaging plane and around the subject. X-ray sources typically include x-ray tubes, which emit the x-ray beam at a focal point. In typical single energy applications, X-ray detectors typically include a collimator for collimating x-ray beams received at the detector, a scintillator for converting x-rays to light energy adjacent the collimator, and photodiodes for receiving the light energy from the adjacent scintillator and producing electrical signals therefrom. Typically, each scintillator of a scintillator array converts x-rays to light energy. Each scintillator discharges light energy to a photodiode adjacent thereto, and each photodiode detects the light energy and generates a corresponding electrical signal. The outputs of the photodiodes are then transmitted to the data processing system for image reconstruction.

A CT imaging system may also include an energy sensitive (ES), multi-energy (ME), and/or dual-energy (DE) CT imaging system that may be referred to as an ESCT, MECT, and/or DECT imaging system, in order to acquire data for material decomposition or effective Z or monochromatic image estimation using multiple energy spectra. ESCT/MECT/DECT provides energy discrimination. For example, in the absence of object scatter, the system derives the material attenuation at a different energy based on the signal from two relative regions of photon energy from the spectrum: the low-energy and the high-energy portions of the incident x-ray spectrum.

In a given energy region relevant to medical CT, two physical processes dominate the x-ray attenuation: (1) Compton scatter and the (2) photoelectric effect. These two processes are sensitive to the photon energy and hence each of the atomic elements has a unique energy sensitive attenuation signature. Therefore, the detected signals from two energy regions provide sufficient information to resolve the energy dependence of the material being imaged in order to enable material decomposition. Such systems may use a direct conversion detector material in lieu of a scintillator. Or, in an alternative, a conventional scintillator-based third-generation CT system may be used to provide energy separation measurements by acquiring projections sequentially at different peak kilovoltage (kVp) operating levels of the x-ray tube, which changes the peak and spectrum of energy of the incident photons comprising the emitted x-ray beams. A principle objective of scanning with two distinctive energy spectra (i.e., dual energy) is to obtain diagnostic CT images that enhance information (contrast separation, material specificity, etc.) within the image by utilizing two scans at different polychromatic energy states.

CT systems having an amount of z-coverage that is equal or less than 10 mm (at isocenter), for instance, typically do not use a scatter correction algorithm. However, in recent years CT systems have increasing z-coverage in order to shorten scan times and reduce overall dose. The goal has been to obtain an image of an object, such as a cardiac region, in a single rotation. As CT systems have grown in z-coverage (i.e., increased numbers of slices), however, scatter has become an increasingly significant factor. For example, for a 16-slice scanner with 10 mm z-coverage, the scatter-to-primary ratio (SPR) is less than 10% for a 35 cm poly phantom. When the z-coverage increases to 40 mm (or 64 slices), the SPR increases to 20% for the same size phantom. And, in a 160 mm wide-cone system, SPR can reach 28% for large objects and a typical 1D anti-scatter grid, or 8% with a 2D anti-scatter grid. It is well-known that an increased SPR degrades image quality due to image artifact and contrast loss.

The amount of scatter in a CT system also depends in part on an amount of energy in the projection beam. Thus, for lower energy applications, below 80 kVp for instance, SPR is greater than for higher energy applications, further exacerbating the issue of scatter and the ability to correct for it. Thus, inherent in a dual energy application, scatter (particularly at the low kVp operation of a dual energy procedure) correction may be necessary, moreso for the low kVp data of such an operation.

Many attempts have been made in the past to improve the scatter performance of CT systems. For example, hardware improvements may be implemented by increasing the aspect ratio of post-patient collimation plates, significantly improving the amount of scatter rejection. The aspect ratio for a collimator is typically defined as the collimator plate height (H) divided by the aperture width (W). In general, the higher the aspect ratio, the better is the scatter rejection capability. However, such solutions tend to be expensive, may limit performance, and may increase an amount of dose required to obtain adequate image data. Thus, in addition to hardware solutions to limit scatter, scatter correction methods have been developed as wider coverage CT systems have been developed.

Generally, there are two types of scatter correction for cone-beam CT: 1) direct correction in x-ray projection space, or 2) using a second pass algorithm using reconstructed images.

When correcting in projection space, known solutions include estimating scatter in projection data using an empirical function (such as a square root function). Such solutions may be computationally attractive, but may have limitations that are exacerbated in wider z-coverage and low energy applications. Typically, such solutions are not accurate for non-uniform objects. Also, assuming a constant empirical function correction may not accurately predict scatter intensity across various scan conditions, and in some applications the amplitude of an estimated scatter profile has to be reduced in order to meet image quality requirements. Further, estimations assuming a constant correction value do not take into account scatter related to a bowtie filter.

When correcting in image space, some known solutions for scatter correction include estimating an amount of scatter based on images and using, for instance, a Monte Carlo application. In this approach, scatter profiles are computed by tracking rays through a reconstructed volume. One known solution includes estimating a size of an image and then performing a scatter correction based on the estimation. However, correcting in image space takes much longer computational time when compared to the first approach, above, which is compounded as wider coverage systems are developed.

Therefore, it would be desirable to design an apparatus and method for improving scatter correction for CT imaging.

BRIEF DESCRIPTION OF THE INVENTION

The invention is a directed method and apparatus for improving scatter correction in CT imaging.

According to one aspect, a CT system includes a rotatable gantry having an opening to receive an object to be scanned, an x-ray source configured to project an x-ray beam toward the object having a primary intensity, a detector configured to detect high frequency electromagnetic energy passing through the object and output imaging data, and a data acquisition system (DAS) connected to the detector and configured to receive the imaging data. The system also includes a computer programmed to obtain image projection data of the object from the DAS, correct the projection data using a scatter function that is based at least on a known characteristic of the x-ray beam, and generate images using the corrected projection data.

According to another aspect, a method of reconstructing an image includes scanning an object to obtain image projection data using an x-ray beam, estimating a scatter profile based on a known characteristic of the x-ray beam, and reconstructing an image of the object using the obtained image projection data and based on the estimated scatter profile.

According to yet another aspect, a non-transitory computer readable storage medium having stored thereon a computer program comprising instruction which, when executed by a computer, cause the computer to obtain scanning information of an object using an x-ray beam, estimate a scatter correction function that is a function of a known characteristic of the x-ray beam, and reconstruct an image of the obtained scanning information based on the estimated scatter correction function.

Various other features and advantages will be made apparent from the following detailed description and the drawings.

BRIEF DESCRIPTION OF THE DRAWINGS

The drawings illustrate preferred embodiments presently contemplated for carrying out the invention.

In the drawings.

DETAILED DESCRIPTION OF THE PREFERRED EMBODIMENT

The operating environment of the invention is described with respect to a sixty-four-slice computed tomography (CT) system. However, it will be appreciated by those skilled in the art that the invention is equally applicable for use with other multi-slice configurations. Moreover, the invention will be described with respect to the detection and conversion of x-rays. However, one skilled in the art will further appreciate that the invention is equally applicable for the detection and conversion of other high frequency electromagnetic energy. The invention will be described with respect to a "third generation" CT scanner, but is equally applicable with other CT systems.

Figure 1:
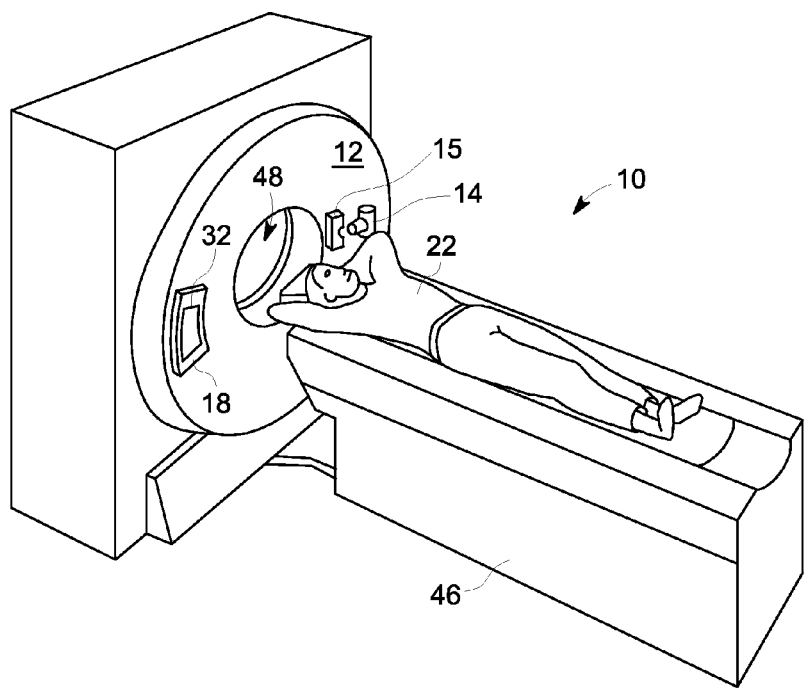
FIG. 1 is a pictorial view of a CT imaging system.
Figure 2:
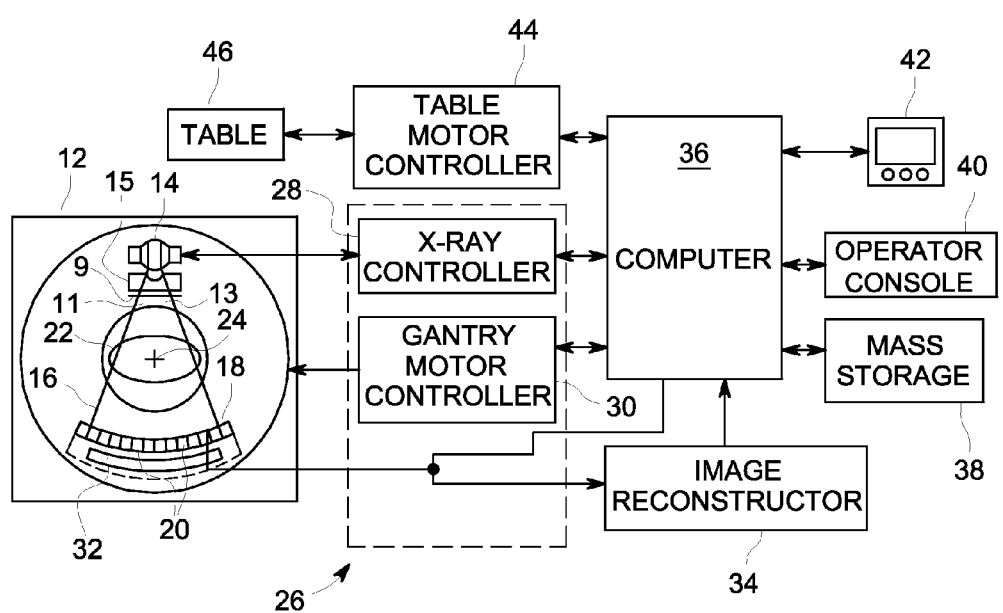
FIG. 2 is a block schematic diagram of the system illustrated in FIG. 1.

Referring to FIGS. 1 and 2, a computed tomography (CT) imaging system 10 is shown as including a gantry 12 representative of a "third generation" CT scanner. Gantry 12 has an x-ray source 14 that projects a beam of x-rays through a bowtie filter 15 and toward a detector assembly or collimator 18 on the opposite side of the gantry 12. In an alternative embodiment, system 10 may include a flat filter 9, either in lieu of bowtie filter 15, or in conjunction therewith. Referring now to FIG. 2, detector assembly 18 is formed by a plurality of detectors 20 and data acquisition systems (DAS) 32. The plurality of detectors 20 sense the projected x-rays 16 that pass through a medical patient 22, and DAS 32 converts the data to digital signals for subsequent processing. Each detector 20 produces an analog electrical signal that represents the intensity of an impinging x-ray beam and hence the attenuated beam as it passes through the patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to an x-ray source 14 and a gantry motor controller 30 that controls the rotational speed and position of gantry 12. An image reconstructor 34 receives sampled and digitized x-ray data from DAS 32 and performs high speed reconstruction. The reconstructed image is applied as an input to a computer 36 which stores the image in a mass storage device 38.

Computer 36 also receives commands and scanning parameters from an operator via console 40 that has some form of operator interface, such as a keyboard, mouse, voice activated controller, or any other suitable input apparatus. An associated display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 and gantry 12. Particularly, table 46 moves patients 22 through a gantry opening 48 of FIG. 1 in whole or in part.

Figure 3:
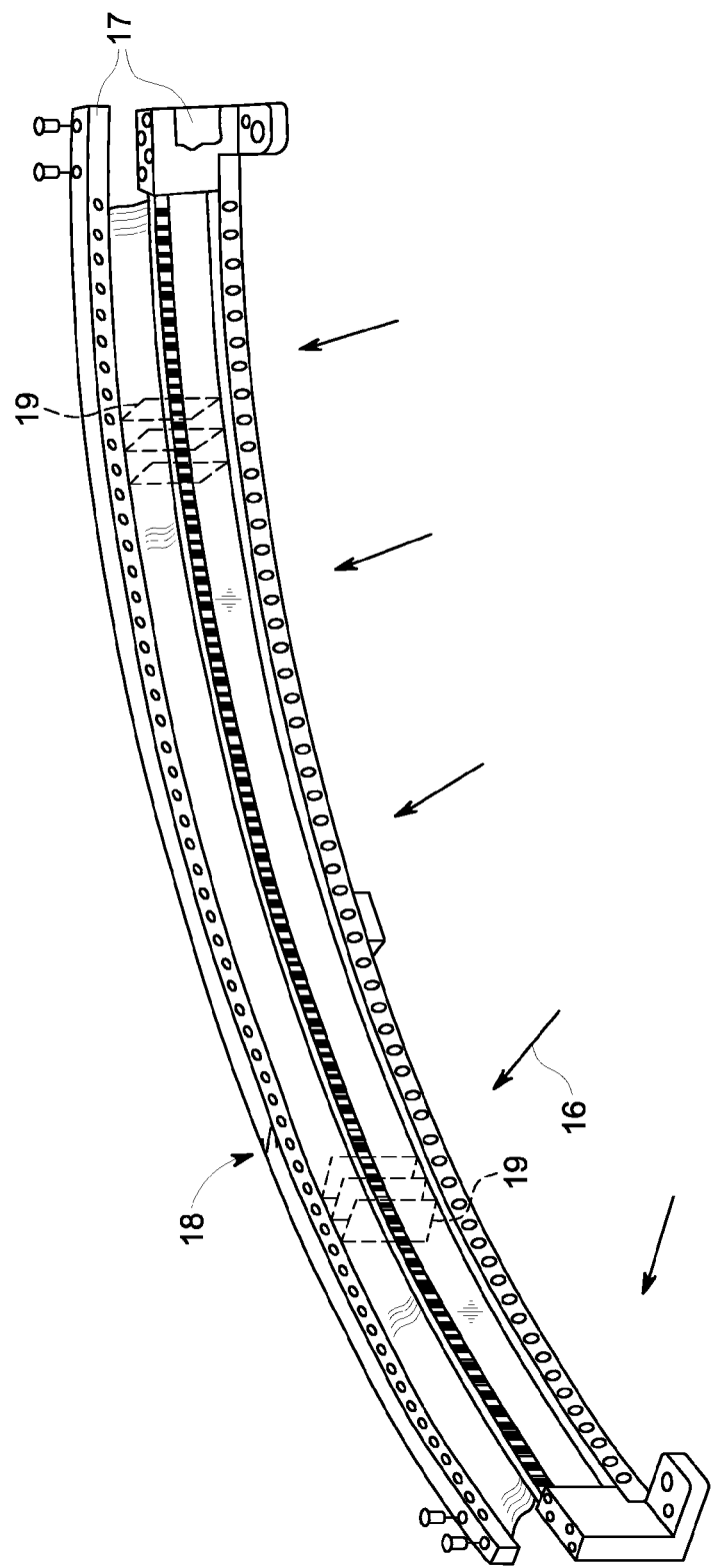
FIG. 3 is a perspective view of one embodiment of a CT system detector array.

As shown in FIG. 3, detector assembly 18 includes rails 17 having collimating blades or plates 19 placed therebetween, thus providing, as known in the art, an amount of coverage in a z-direction (or slice direction) which corresponds to a length in the z-direction of plates 19 and, correspondingly, a length in the z-direction of detectors 20. Plates 19 are positioned to collimate x-rays 16 before such beams impinge upon, for instance, detector 20 of FIG. 4 positioned on detector assembly 18. In one embodiment, detector assembly 18 includes 57 detectors 20, each detector 20 having an array size of 64×16 of pixel elements 50. As a result, detector assembly 18 has 64 rows and 912 columns (16×57 detectors) which allows 64 simultaneous slices of data to be collected with each rotation of gantry 12. Further, as known in the art, an aspect ratio of detector assembly may be calculated using a spacing between plates 19 and their length in the z-direction.

Figure 4:
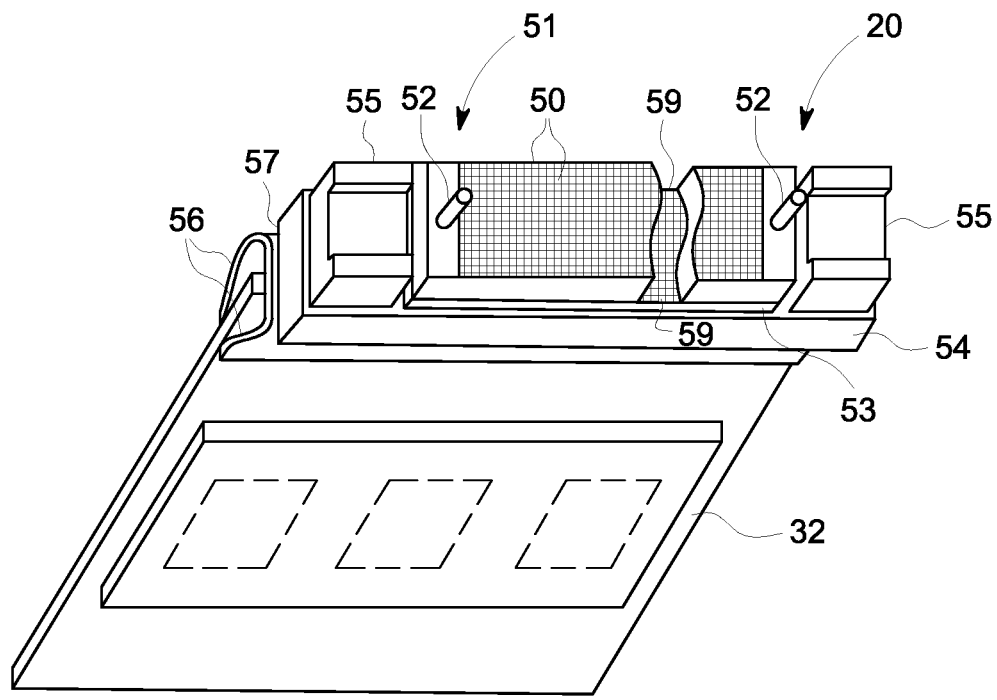
FIG. 4 is a perspective view of one embodiment of a detector.

Referring to FIG. 4, detector 20 includes DAS 32, with each detector 20 including a number of detector elements 50 arranged in pack 51. Detectors 20 include pins 52 positioned within pack 51 relative to detector elements 50. Pack 51 is positioned on a backlit diode array 53 having a plurality of diodes 59. Backlit diode array 53 is in turn positioned on multi-layer substrate 54. Spacers 55 are positioned on multi-layer substrate 54. Detector elements 50 are optically coupled to backlit diode array 53, and backlit diode array 53 is in turn electrically coupled to multi-layer substrate 54. Flex circuits 56 are attached to face 57 of multi-layer substrate 54 and to DAS 32. Detectors 20 are positioned within detector assembly 18 by use of pins 52.

In the operation of one embodiment, x-rays impinging within detector elements 50 generate photons which traverse pack 51, thereby generating an analog signal which is detected on a diode within backlit diode array 53. The analog signal generated is carried through multi-layer substrate 54, through flex circuits 56, to DAS 32 wherein the analog signal is converted to a digital signal as image projection data. Other embodiments include, in lieu of pack 51 and backlit diode array 53, photon counting or direct conversion detectors as detector elements 50, providing an ability to resolve energy in the imaging data.

According to the invention, an x-ray spectrum from a single energy may be applied to x-ray source 14 of FIGS. 1 and 2, and projection data may be obtained and images reconstructed in a conventional CT imaging application using x-rays 16. However, in an alternate embodiment, dual energies or multiple energies may be applied to x-ray source 14, illustrated as x-rays 11 and x-rays 13 in FIG. 2 (which correspond generally to a location of x-rays 16). In one embodiment, x-rays 11 are generated at a first x-ray energy of for instance 80 kVp, and x-rays 13 are generated at a second x-ray energy of for instance 140 kVp. However, it is contemplated that any combination of low and high kVp x-ray energies may be utilized for image data generation, according to the invention.

As x-ray source 14 and detector array 18 rotate, detector array 18 collects data of attenuated x-ray beams 11, 13 (in a dual-energy application) or of attenuated x-rays 16 (in a single-energy application). Data collected by detector array 18 undergoes pre-processing and calibration to condition the data to represent line integrals of attenuation coefficients of scanned object or patient 22. The processed data are commonly called projections. For dual energy applications, two or more sets of projection data are typically obtained for an imaged object at different tube peak kilovoltage (kVp) levels, which change a peak and spectrum of energy of incident photons comprising emitted x-ray beams. The acquired sets of projection data may be used for, for instance, basis material decomposition (BMD), or other techniques, as known in the art.

Figure 5:
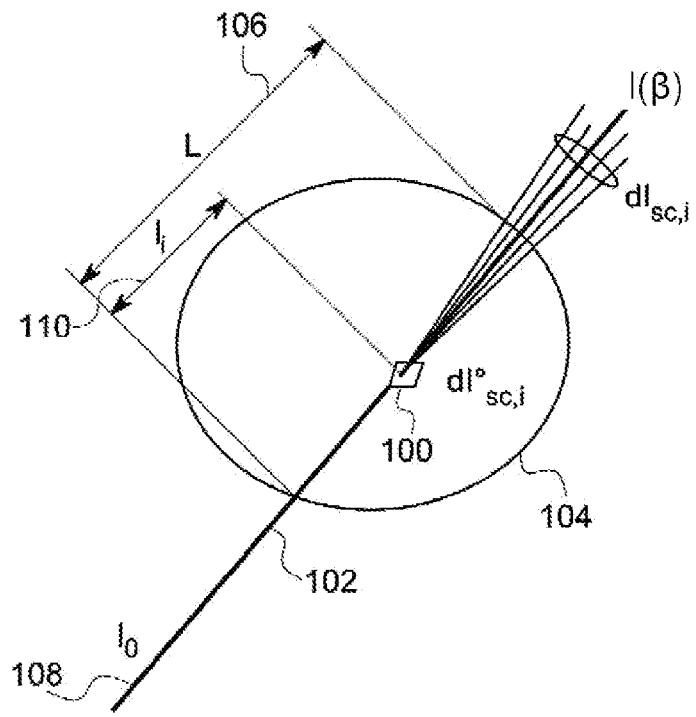
FIG. 5 is a forward scatter intensity model for illustrating derivation of elements related to the invention.

On clinical CT systems with either one-dimensional (1D) or two-dimensional (2D) anti-scatter grids, the majority of scattered photons reached at detector is from forward scattering (or small angle scattering). Scatter correction based only upon projection data is, then, to determine the forward scatter intensity distribution. As shown in FIG. 5, a certain voxel i 100 on the path of x-ray 102 through object 104 having x-ray attenuation $\mu_i$ along extension dl (along length L 106) is the source of forward scatter intensity:

$$dI_{sc,i}^o \propto \overline{K_{sc,f,i}} \cdot \mu_i \cdot I_o \cdot \exp\left(-\int_0^{l_i} \mu(\lambda)\, d\lambda\right) dl, \qquad \text{Eqn. 1.}$$

As shown in Eqn. 1 and still referring to FIG. 5, the differential forward scatter intensity is proportional to several terms, that include the primary intensity $I_o$ 108 emitted by the x-ray source 14. The forward scatter constant $\overline{K_{sc,f,i}}$ refers to the mean differential scatter cross section of voxel element i 100 for scatter angle $\psi \approx 0$. The exponential term of Eqn. 1 represents an amount of attenuation of the unattenuated primary intensity $I_o$ 108 through a distance $l_i$ 110 in the object. The forward scattered intensity leaving the voxel element i 100 is attenuated through the remaining distance $L-l_i$ through object 104. Eqn. 2 proportionately represents the forward scatter intensity emitted by the voxel i 100 that reaches to the corresponding detector.

$$dI_{sc,i} \propto \overline{K_{sc,f,i}} \cdot \mu_i \cdot I_o \cdot \exp\left(-\int_0^{l_i} \mu(\lambda)\, d\lambda\right) \cdot \exp\left(-\int_{l_i}^{L} \mu(\lambda)\, d\lambda\right) dl, \qquad \text{Eqn. 2.}$$

As shown in Eqn. 3, integrating the differential forward scatter intensities along the ray path [0, L] through object 104 yields the total forward scatter intensity detected in the corresponding detector channel, $$I_{sc} \propto \int_0^L \overline{k_{sc,f}}(l)\, dl \cdot I_o \cdot \exp\left(-\int_0^L \mu(\lambda)\, d\lambda\right) \cdot \int_0^L \mu(l)\, dl, \qquad \text{Eqn. 3.}$$

Eqn. 3 can be further simplified into the following form:

$$I_{sc}(\beta) \propto \int_0^L \overline{k_{sc,f}}(l)\, dl \cdot I(\beta) \cdot \left(-\ln\frac{I(\beta)}{I_o}\right), \qquad \text{Eqn. 4.}$$

Eqn. 4 thus illustrates that the scatter intensity is proportional to a weighted product of the measured intensity and the corresponding object size along the beam path. Traditionally, as noted above, the weighting factor $$\int_0^L \overline{k_{sc,f}}(l)\, dl$$

of Eqn. 4 is treated as a constant scale factor. However, such treatment is not able to accurately predict scatter intensity across various scan conditions, scatter for wider scanning applications in z, and scatter for non-uniform imaging objects.

Figure 6:
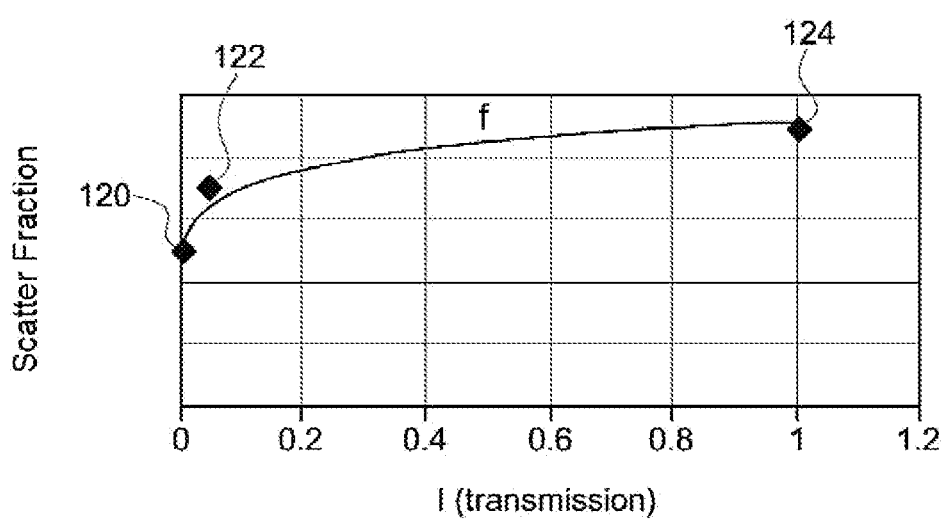
FIG. 6 is an example of an adaptive function for scatter correction having an exemplary curve fit.

Thus, scatter may be modeled and accounted for according to the invention and as described herein. The integral of scatter cross section along the beam path, $$\int_0^L \overline{k_{sc,f}}(l)\, dl,$$

is modeled as a function of the measured intensity $I(\beta)$. This derives from the fact that the measured intensity $I(\beta)$ is lower if there are high attenuating materials in the beam path, and I(β) is higher if there tend to be low attenuating materials in the beam path. Therefore, Eqn. 4 is modified into the following form:

$$I_{sc}(\beta) \propto (I(\beta))^{f(I(\beta))} \cdot \left(-\ln\frac{I(\beta)}{I_o}\right), \qquad \text{Eqn. 5,}$$

wherein $f(I(\beta))$ is called the adaptive function, which can be calibrated from measurements and then used for subsequent imaging sessions wherein the scatter function may be generated as a profile for correcting projection data of an object. An example of $f(I(\beta))$ is shown in FIG. 6 which is dimensionless in the y-direction and represents an amount of scatter at a given transmission. The curve illustrated therein is generated using calibration acquisitions, which are generated for different objects (i.e., different materials)—hence the amount of transmission varies, accordingly. The response, or measured scatter function, is thereby representative of small angle scatter and effectively enables scatter correction that is physics based—dependent on such factors such as system geometry, source characteristics (spectrum, energy, etc.), and collimation, as examples.

Thus, referring still to the example of FIG. 6, scatter data is obtained for two or more materials (three materials are illustrated in FIG. 6: first material 120, second material 122, and third material 124) and, using the obtained scatter data, the adaptive function $f(I(\beta))$ can be generated, as illustrated in the curve fit equation. According to one embodiment, the data obtained for adaptive function $f(I(\beta))$ is modeled as a power function of the form $f(I(\beta))=C(I(\beta))^d$, where C and d are empirically derived constants from data such as materials 120-124. Thus, as known in the art, if the form of the curve fit is known or assumed, then two material measurements are adequate to provide the function information and corresponding constants, such as constants C and d of power function $f(I(\beta))=C(I(\beta))^d$.

Figure 7:
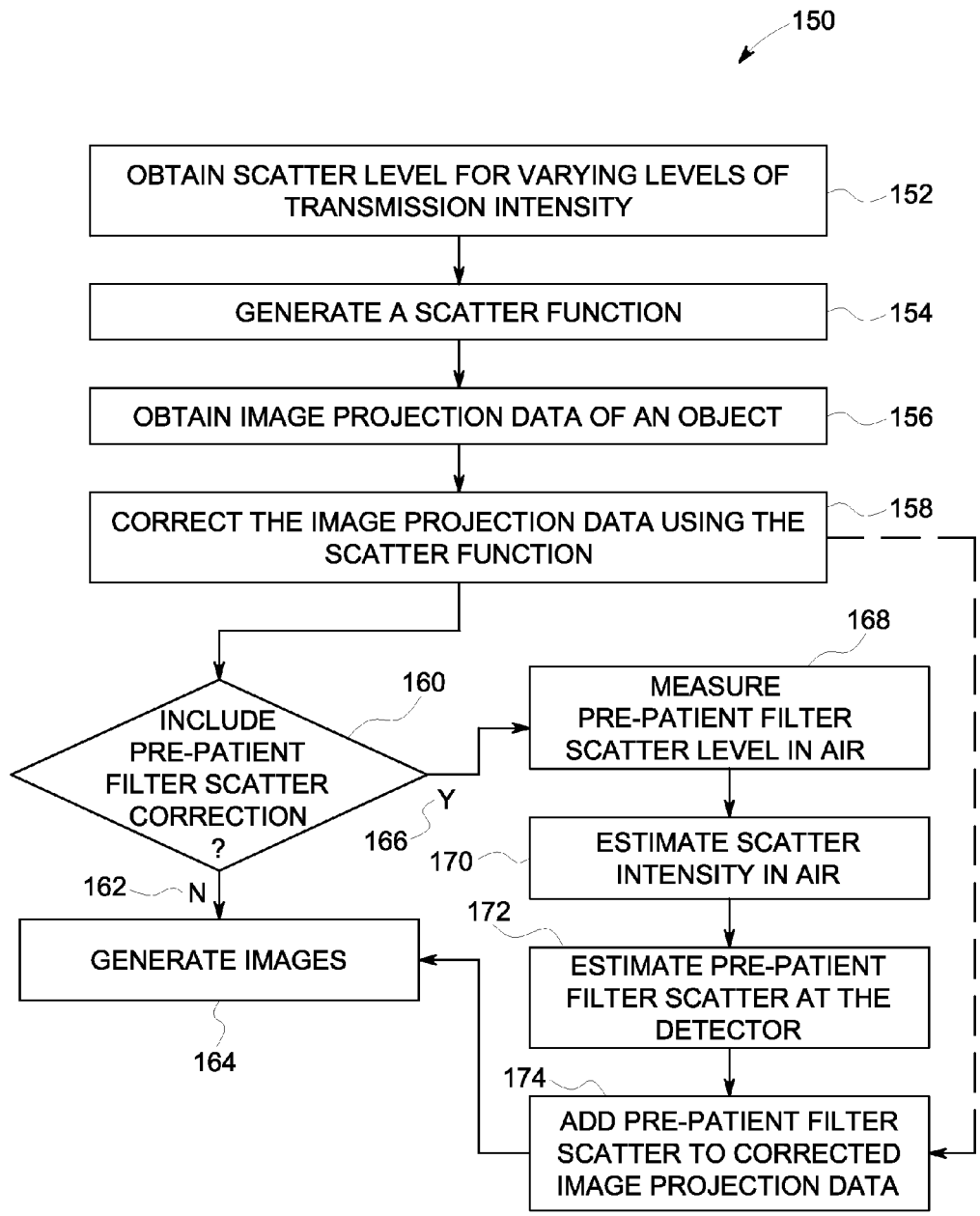
FIG. 7 illustrates a method for correcting scatter in image projection data, according to the invention.

According to the invention, bowtie scatter may be taken into account, which is often ignored in traditional scatter correction. The steps to add bowtie scatter into the scatter profile include the following:

1) Measure bowtie scatter level (SPR) in air scan, an example of which is shown in FIG. 7.

2) Estimate bowtie scatter intensity in air scan:

$$I_{sc,bowtie}^{air}=I_o^{air} \cdot SPR_{bowtie}/(1+SPR_{bowtie}), \qquad \text{Eqn. 6.}$$

3) Estimate bowtie scatter reached at detector:

$$I_{sc,bowtie}^{air} \cdot \exp\left(-\int_0^L \mu(l)dl\right) = \qquad \text{Eqn. 7.}$$

$$I_{sc,bowtie}^{air} \cdot \frac{I(\beta)}{I_o^{air}} = I(\beta) \cdot SPR_{bowtie}/(1+SPR_{bowtie}),$$

Because bowtie scatter behaves like a secondary x-ray source, the angle β may be defined as a small angle range [β−Δβ, α+Δβ].

4) Add bowtie scatter to the total scatter intensity profile.

As such, according to the invention and referring to FIG. 7, a method 150 for correcting scatter includes obtaining scatter level for varying levels of transmission intensity 152. As discussed and illustrated above with respect FIG. 6, an amount of scatter is obtained for varying levels of transmission intensity. At step 154, the scatter level data is plotted as a function of transmission intensity and a curve fit routine (or other known methods for representing empirically derived data) is applied thereto in order to obtain the scatter or adaptive function $f((\beta))$. At step 156, image projection data of an object is obtained, and the image projection data is corrected using the scatter or adaptive function is generated $f((\beta))$, at step 158.

Further, according to the invention, estimating the scatter profile is not limited to the method illustrated in FIG. 7, but may include estimating based on such things as the x-ray spectrum, use of the bowtie filter or the flat filter, an amount of x-ray beam coverage in a z-direction (or slice direction), or based on the post-patient collimator aspect ratio, as examples.

According to the invention, the image projection data may be further corrected by accounting for scatter in the bowtie filter, or such step may be foregone and images may be generated using the corrected image projection data obtained at step 158. Thus, at step 160, if no bowtie scatter correction 162, then images are generated 164. However, if bowtie scatter correction is included 166, then as described, bowtie scatter level is measured in air 168, scatter intensity for the bowtie is estimated in air 170, and bowtie scatter at the detector is estimated 172. The estimated bowtie scatter at the detector is added to the corrected image projection data 174, and images are generated 164. Thus, images may be generated at step 164 having image projection data corrected using a scatter function, according to the invention, and in one embodiment, scatter from the bowtie filter is included in the correction of the image projection data in the final images.

It is to be understood that the steps of method 150 need not be limited to the sequential order presented therein. Instead, according to the invention, data may be obtained in alternate or differing orders while adhering to the spirit of the invention. For instance, step 168 includes the step of measuring bowtie scatter level in air, then estimating bowtie scatter intensity in air and estimating bowtie scatter at the detector 170, 172. However, according to another embodiment, step 168 may instead be executed at a point in the sequence when, for instance, the scatter level for varying levels of transmission data is obtained, step 152. That is, the step of measuring the bowtie scatter level in air 168 may be performed prior to obtaining image projection data of the object at step 156, as an example.

Figure 8:
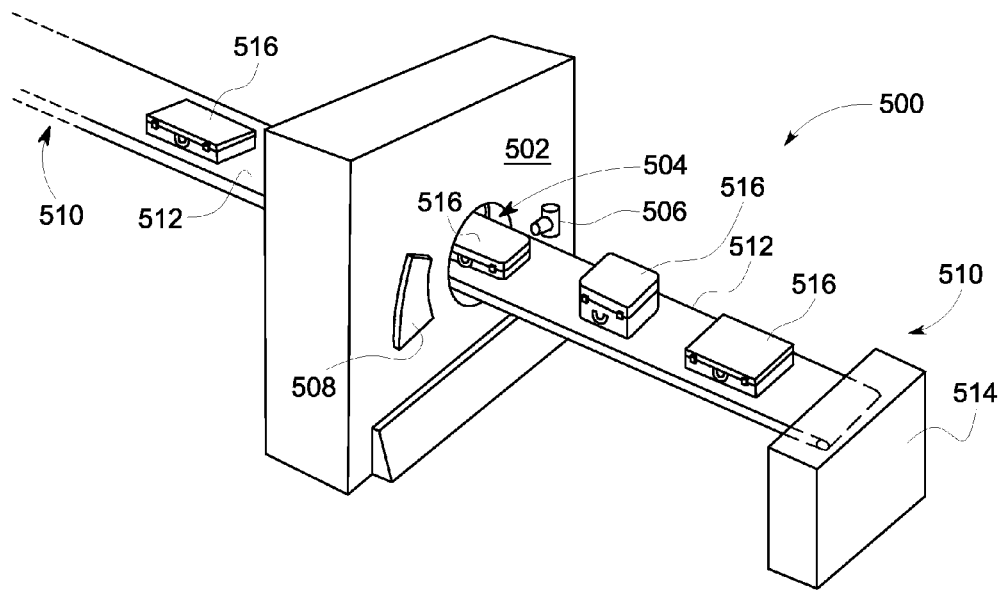
FIG. 8 is a pictorial view of a CT system for use with a non-invasive package inspection system.

Referring now to FIG. 8, package/baggage inspection system 500 includes a rotatable gantry 502 having an opening 504 therein through which packages or pieces of baggage may pass. The rotatable gantry 502 houses a high frequency electromagnetic energy source 506 as well as a detector assembly 508 having scintillator arrays comprised of scintillator cells similar to that shown in FIG. 3 or 4. A conveyor system 510 is also provided and includes a conveyor belt 512 supported by structure 514 to automatically and continuously pass packages or baggage pieces 516 through opening 504 to be scanned. Objects 516 are fed through opening 504 by conveyor belt 512, imaging data is then acquired, and the conveyor belt 512 removes the packages 516 from opening 504 in a controlled and continuous manner. As a result, postal inspectors, baggage handlers, and other security personnel may non-invasively inspect the contents of packages 516 for explosives, knives, guns, contraband, etc.

A technical contribution for the disclosed method and apparatus is that it provides for a computer implemented method and apparatus for adaptive scatter correction in an imaging system.

One skilled in the art will appreciate that embodiments of the invention may be interfaced to and controlled by a computer readable storage medium having stored thereon a computer program. The computer readable storage medium includes a plurality of components such as one or more of electronic components, hardware components, and/or computer software components. These components may include one or more computer readable storage media that generally stores instructions such as software, firmware and/or assembly language for performing one or more portions of one or more implementations or embodiments of a sequence. These computer readable storage media are generally non-transitory and/or tangible. Examples of such a computer readable storage medium include a recordable data storage medium of a computer and/or storage device. The computer readable storage media may employ, for example, one or more of a magnetic, electrical, optical, biological, and/or atomic data storage medium. Further, such media may take the form of, for example, floppy disks, magnetic tapes, CD-ROMs, DVD-ROMs, hard disk drives, and/or electronic memory. Other forms of non-transitory and/or tangible computer readable storage media not list may be employed with embodiments of the invention.

A number of such components can be combined or divided in an implementation of a system. Further, such components may include a set and/or series of computer instructions written in or implemented with any of a number of programming languages, as will be appreciated by those skilled in the art. In addition, other forms of computer readable media such as a carrier wave may be employed to embody a computer data signal representing a sequence of instructions that when executed by one or more computers causes the one or more computers to perform one or more portions of one or more implementations or embodiments of a sequence.

According to one embodiment, a CT system includes a rotatable gantry having an opening to receive an object to be scanned, an x-ray source configured to project an x-ray beam toward the object having a primary intensity, a detector configured to detect high frequency electromagnetic energy passing through the object and output imaging data, and a data acquisition system (DAS) connected to the detector and configured to receive the imaging data. The system also includes a computer programmed to obtain image projection data of the object from the DAS, correct the projection data using a scatter function that is based at least on a known characteristic of the x-ray beam, and generate images using the corrected projection data.

According to another embodiment, a method of reconstructing an image includes scanning an object to obtain image projection data using an x-ray beam, estimating a scatter profile based on a known characteristic of the x-ray beam, and reconstructing an image of the object using the obtained image projection data and based on the estimated scatter profile.

According to yet another embodiment, a non-transitory computer readable storage medium having stored thereon a computer program comprising instruction which, when executed by a computer, cause the computer to obtain scanning information of an object using an x-ray beam, estimate a scatter correction function that is a function of a known characteristic of the x-ray beam, and reconstruct an image of the obtained scanning information based on the estimated scatter correction function.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A Computed Tomography (CT) system comprising:
   a rotatable gantry having an opening to receive an object to be scanned;
   an x-ray source configured to project an x-ray beam toward the object, the x-ray beam having a primary intensity;
   a detector configured to detect energy from the x-ray beam passing through the object and output imaging data;
   a data acquisition system (DAS) connected to the detector and configured to receive the imaging data; and
   a computer programmed to:
      obtain image projection data of the object from the DAS;
      correct the image projection data using a scatter function that is based at least on a known characteristic of the x-ray beam and a characteristic of the object; and
      generate images using the corrected projection data; and
   wherein the scatter function comprises a function of the form $$I(\beta)^{f(I(\beta))} \cdot \left(-\ln\frac{I(\beta)}{I_o}\right)$$

that represents a level of scatter of the x-ray beam as a function of transmission intensity, where $I(\beta)$ is the x-ray beam transmission intensity along the x-ray transmission direction indicated by the angle $\beta$, $f(I(\beta))$ is an adaptive function, and $I_o$ is the primary intensity incident upon the object along a given direction.

2. The system of claim 1 wherein the known characteristic of the x-ray includes one of the primary intensity of the x-ray beam and a spectrum of the x-ray beam.

3. The system of claim 1 comprising an x-ray controller coupled to the x-ray source, the x-ray controller configured to command the x-ray source to output a first x-ray energy and a second x-ray energy that is different from the first x-ray energy.

4. The system of claim 1 wherein the adaptive function is obtained through two or more scatter intensity measurements;
   wherein each of the two or more scatter intensity measurements comprise a level of scatter for a given transmission intensity; and
   wherein each of the two or more scatter intensity measurements is obtained from a different material.

5. The system of claim 1
   wherein the adaptive function is a power function of the form:
   $f(I(\beta))=C(I(\beta))^d$, where C and d are empirically derived constants.

6. The system of claim 1 wherein the scatter function is a physics-based model that accounts for forward scatter and is based on the x-ray beam transmission intensity.

7. The system of claim 1 wherein the scatter function is based on an x-ray beam coverage in a z-direction of the system.

8. The system of claim 1 wherein the scatter function is based on a post-patient collimator aspect ratio.

9. The system of claim 1 wherein the computer is programmed to correct the image projection data based on a measured pre-patient filter scatter level.

10. The system of claim 9 wherein the computer is programmed to:

measure the pre-patient filter scatter level in air;
estimate pre-patient filter scatter reached at the detector based on the measured pre-patient scatter level in air; and
generate the images using the estimated pre-patient filter scatter reached at the detector.

11. The system of claim 10 wherein the pre-patient filter is one of a bowtie filter and a flat filter.

12. A method of reconstructing an image comprising:
acquiring scatter data for a plurality of different materials during a first imaging session;
scanning an object to obtain image projection data using an x-ray beam during a second imaging session, different from the first imaging session;
generating a scatter function from the acquired scatter data;
estimating a scatter profile based on attenuation of the object along the path of the x-ray beam and the scatter function, wherein the scatter function is a function of the form:

$$I(\beta)^{f(I(\beta))} \cdot \left(-\ln\frac{I(\beta)}{I_o}\right),$$

where $I(\beta)$ is the x-ray beam transmission intensity along the x-ray transmission direction indicated by the angle $\beta$, $I_o$ is the primary intensity incident upon the object along a given direction, and $f(I(\beta))$ is an adaptive function, wherein the adaptive function is a power function of the form: $f(I(\beta))=C(I(\beta))^d$, where C and d are empirically derived constants;
correcting the image projection data with the estimated scatter profile; and
reconstructing an image of the object using the corrected image projection data.

13. The method of claim 12 wherein the estimating of the scatter profile is further based on a known characteristic where the known characteristic includes one of a primary intensity of the x-ray beam and a spectrum of the x-ray beam.

14. The method of claim 12 wherein scanning the object comprises scanning the object to obtain the image projection data at a first x-ray energy and a second x-ray energy that is different from the first x-ray energy.

15. The method of claim 12 comprising:
adding a bowtie scatter estimate to the estimated scatter profile, the bowtie scatter estimate comprising an estimate of scatter from a bowtie filter.

16. The method of claim 12 comprising estimating the scatter profile using two or more scatter transmission measurements, wherein the two or more scatter transmission measurements comprise scatter levels corresponding to varying levels of transmission intensity.

17. The method of claim 12 comprising correcting the image projection data using a correction that is based on a measured pre-patient filter scatter level.

18. The method of claim 17 comprising:
measuring the pre-patient filter scatter level in air;
estimating a level of pre-patient filter scatter reached at the detector based on the measured pre-patient filter scatter level in air; and
generating the correction using the estimated level of pre-patient filter scatter reached at the detector.

19. The method of claim 18 wherein the pre-patient filter comprises one of a bowtie filter and a flat filter.

20. A non-transitory computer readable storage medium having stored thereon a computer program comprising instructions which, when executed by a computer, cause the computer to:
acquire scatter information for an x-ray beam, the scatter information comprising scatter levels for varying levels of transmission intensity;
obtain image projection data of an object using the x-ray beam;
estimate a scatter function from the acquired scatter information and an attenuation of the object along the path of the x-ray beam, the scatter function comprising a function of the form $$I(\beta)^{f(I(\beta))} \cdot \left(-\ln\frac{I(\beta)}{I_o}\right),$$

where $I(\beta)$ is the x-ray beam transmission intensity along the x-ray transmission direction indicated by the angle $\beta$, $f(I(\beta))$ is an adaptive function, and $I_o$ is the primary intensity incident upon the object along a given direction;
correct the image projection data using the estimated scatter function; and
reconstruct an image of the object from the corrected image projection data.

21. The non-transitory computer readable storage medium of claim 20 wherein the computer is further caused to estimate the scatter function using one of a primary intensity of the x-ray beam and a spectrum of the x-ray beam.

22. The non-transitory computer readable storage medium of claim 20 wherein the computer is further caused to:
command an x-ray source to output a first x-ray energy and a second x-ray energy that is different from the first x-ray energy; and
obtain the image projection data as dual energy image projection data at both the first x-ray energy and the second x-ray energy.

23. The non-transitory computer readable storage medium of claim 20 wherein the computer is further caused to:
perform two or more scatter intensity measurements, each with different scatter intensities; and
estimate the scatter function based on the two or more scatter intensity measurements; and
wherein each of the two or more scatter intensity measurements are performed on a different material.

24. The non-transitory computer readable storage medium of claim 20
wherein the adaptive function is a power function of the form:
$f(I(\beta))=C(I(\beta))^d$, where C and d are empirically derived constants.

25. The non-transitory computer readable storage medium of claim 20 wherein the computer is further caused to correct the image projection data based on a measured pre-patient filter scatter level.

26. The non-transitory computer readable storage medium of claim 25 wherein the computer is programmed to:
measure the pre-patient filter scatter level in air;
estimate pre-patient filter scatter reached at the detector based on the measured pre-patient filter scatter level in air; and
reconstruct the image using the estimated pre-patient filter scatter reached at the detector.

27. The non-transitory computer readable storage medium of claim 26 wherein the pre-patient filter is one of a bowtie filter and a flat filter.

\* \* \* \* \*